United States Patent [19]
Axelgaard

[11] Patent Number: 5,263,481
[45] Date of Patent: Nov. 23, 1993

[54] ELECTRODE SYSTEM WITH DISPOSABLE GEL

[76] Inventor: Jens Axelgaard, 811 Tumbleweed La., Fallbrook, Calif. 92028-9447

[21] Appl. No.: 887,690

[22] Filed: May 21, 1992

[51] Int. Cl.$^5$ .............................................. A61B 5/04
[52] U.S. Cl. .................................. 128/640; 128/639; 128/643; 607/149
[58] Field of Search ............................. 128/639–641, 128/643, 644, 783, 798, 802, 421

[56] References Cited

U.S. PATENT DOCUMENTS

| | | | |
|---|---|---|---|
| 4,121,575 | 10/1978 | Mius et al. | 128/644 |
| 4,381,012 | 4/1983 | Russek | 128/802 |
| 4,390,023 | 6/1983 | Rise | 128/419 |
| 4,580,572 | 4/1986 | Granek | 128/689 |
| 4,583,547 | 4/1986 | Granek | 128/639 |
| 4,595,013 | 6/1986 | Jones et al. | 128/639 |
| 4,729,377 | 3/1988 | Granek | 128/639 |
| 4,777,954 | 10/1988 | Keusch et al. | 128/641 |
| 4,830,776 | 5/1989 | Thompson | 252/500 |
| 4,837,049 | 6/1989 | Byers et al. | 427/96 |
| 4,854,323 | 8/1989 | Rubin | 128/644 |
| 4,909,260 | 3/1990 | Salem et al. | 128/721 |
| 4,911,169 | 3/1990 | Ferrari | 128/641 |
| 4,928,690 | 5/1990 | Heilman et al. | 128/421 |
| 4,955,381 | 9/1990 | Way et al. | 128/640 |
| 5,016,629 | 5/1991 | Kanare | 128/402 |
| 5,038,797 | 8/1991 | Baiters | 128/798 |

Primary Examiner—Stephen C. Pellegrino
Assistant Examiner—Michael Peffley
Attorney, Agent, or Firm—Walter A. Hackler

[57] ABSTRACT

An electrode system includes a nonconductive material and straps for positioning and holding the nonconductive material against a body part. Flexible conductive fabric patches are attached to the nonconductive material along with lead wires for electrically connecting the fabric patches to a remote monitor or pulse generator. An electrically conductive adhesive gel pad is provided for releasably coupling the flexible conductive fabric patch to the body part. The pad is selectively removable from the fabric patch, enabling removal of the patch from the gel pad while the latter remains adhered to a body part. This facilitates release of the conductive fabric patch and separate disposal of the adhesive gel pad.

23 Claims, 2 Drawing Sheets

ELECTRODE SYSTEM WITH DISPOSABLE GEL

The present invention generally relates to an electrode system enabling repeated use of gel-free electrodes and is useful for both monitoring electrical impulses and providing electrical impulses to a body depending upon the size of the electrode, among other factors.

As an example, electrocardiograph (EKG) and electroencephalograph (EEG) devices for monitoring electrical impulses generally require small contact surfaces with a patient's skin.

On the other hand, transcutaneous electrical nerve stimulation (TENS), electrical muscle stimulation (EMS), and functional electrical stimulation (FES) generally require larger skin surface contact to effect proper stimulation.

Transcutaneous electrical nerve stimulation is useful, for example, in post-operative and chronic pain control, while muscle stimulation is useful, for example, in maintenance and development of muscle tissue.

Electrodes suitable for use in nerve and muscle stimulation preferably provide a uniform electrical coupling across the skin for electrical interface.

Prior art electrodes have utilized a number of conductive elements, such as carbon impregnated rubber and vinyl, as well as metallic foils.

However, a useful electrode must be flexible in order to accommodate relative movement of the patient's skin therebeneath.

In order to electrically couple the electrode to the skin, prior art devices have utilized many types of conductive electrolytes, both in the form of fluids and gels.

One type of electrode used for temporary application of muscle stimulation includes a flat, smooth contacting surface and a separate conductive grease or gel is applied to the skin to electrically couple the electrode thereto. Experience with this system has shown that the grease or gel is messy to use and remove and the electrodes are not suitable for curved body parts. After use the grease or gel must be cleaned or washed from the skin and electrode.

Another type of electrode most suitable for longer term application of electrical stimulation or monitoring includes a flexible conductive fabric or material.

Typically, this type of electrode includes an electrically conductive woven, knit or mesh material with a gel electrolyte impregnated therein in order to improve electrical conduction within the electrode.

In most instances, this conductive gel is adhesive in nature so that it may perform a dual function by both electrically coupling the electrode to the body and adhering the electrode to the body. A typical electrode of this kind is disclosed in U.S. Pat. Nos. 4,708,149 and 4,722,354. These electrodes include a conductive fabric with a flexible conductive adhesive disposed on one side of the conductive fabric for adhering the flexible transcutaneous electrical nerve and/or muscle stimulation electrode to the skin of a patient.

While this type of electrode is effective, a great number of electrodes may be required to provide long term treatment for certain injuries, such as those incurred in sports.

Since most of the known electrodes are disposable in nature and useful for only relatively short periods of time, due to removal for body hygiene, a considerable expense may be anticipated in the treatment of a patient.

The present invention is directed to an economical electrode system in which the basic electroconducting and electrical distribution portion of the electrode is reusable and, in fact, washable. In combination therewith and in accordance with the present invention, a separate adhesive electrically conductive pad is used to couple the "dry" electrode to the skin. Thus, only an expendable gel pad material need be disposable throughout the treatment of the patient. In addition, one embodiment of the present invention also enables the use of a plurality of electrodes, which may be of diverse size, in combination with a support member with spacing between electrodes selected and adjusted as may be preferred, depending on the use and application of the system.

SUMMARY OF THE INVENTION

An electrode system, in accordance With the present invention, generally includes a nonconductive material and means for positioning and holding the nonconductive material against a body part.

A flexible conductive patch, attached to the nonconductive material is electrically connected to a monitor or an electrical stimulator by means of a lead wire. More particularly, a plurality of flexible conductive patches may be attached to the nonconductive material, each being separately connected to electrical lead wires. The nonconductive material ad the flexible conductive patches may be formed from a washable material, thus enabling repeated reuse of this equipment of the electrode system in accordance with the present invention.

In one embodiment of the present invention the nonconductive material may be an elastic fabric for enabling relative independent placement of the conductive patches, which may also be a fabric material, on a body while maintaining the convenience of an electrode set on one substrate. This arrangement facilitates placement of the electrode set onto a body.

In another embodiment of the present invention, the nonconductive material may include a pile type fabric or material, and the conductive patches may include a hook type fabric to enable placement and removal of the conductive patches from the nonconductive material. This arrangement enables electrodes of different sizes to be used in combination with spacing therebetween, selected to meet specific stimulation or monitoring needs.

Importantly, the present invention includes an electrically conductive gel for releasably coupling the flexible conductive fabric patch to the body part with the electrically conductive gel being removable from the flexible conductive fabric patch. Thus, the conductive gel in accordance with the present invention is a separate and disposable item.

More particularly, the electrically conductive gel in accordance with the present invention includes means for enabling the gel to adhere more to the body part than to the flexible conductive fabric patch, thereby enabling the flexible conductive fabric patch and attached nonconductive fabric to be removed from the body part, while leaving the electrically conductive gel adhered to the body part. This facilitates removal of the fabric patch without the necessity of scraping or separating the conductive gel therefrom. Since the conductive gel is not disposed within interstices of the fabric and bound to the fabric, a clean separation of the patch from the conductive gel is effected. In addition, because the gel has dimensional integrity, it cleanly separates from the body part. Hence, no separate cleaning or washing of the body part is necessary as is required by prior art devices.

More specifically, the means for causing the electrically conductive gel means to adhere more to the body part comprises a flexible mesh disposed within the electrically conductive gel. The adhesive characteristic of the gel is created by disposing the flexible mesh Within the gel closer to one surface than another opposing surface, with the one surface being used to adhere the flexible conductive fabric patch to the nonconductive fabric.

Importantly, the flexible mesh also functions to provide dimensional stability to the gel and therefore facilitate handling and removal of the gel from a body without fragmentation thereof. In addition the flexible mesh provides increase gel integrity which also facilitates handling and storage thereof.

To facilitate manufacture of the present invention, the flexible conductive fabric patch may be sewn to the nonconductive fabric and the lead wire includes a plurality of electrically conductive strands with the latter sewn to the flexible conductive fabric patch.

Alternatively, the conductive fabric patch may be glued to the nonconductive fabric and the lead wire glued to the conductive fabric patch.

BRIEF DESCRIPTION OF THE DRAWING

The advantages and features of the present invention will be better understood by the following description when considered in conjunction with the accompanying drawings in which:

FIG. 4 is a cross-sectional representation of a gel pad shown in FIG. 1 showing a mesh disposed therein;

DETAILED DESCRIPTION

Figure 5:
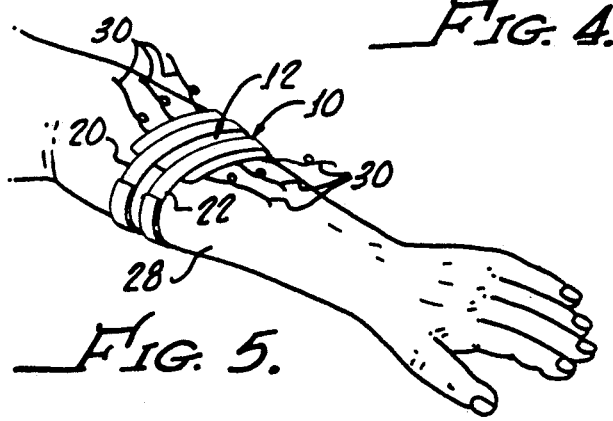
FIG. 5 is perspective view of the embodiment shown in FIG. 1 as it may be disposed on a body part.

Turning now to the figures, there is shown an electrode system 10 which generally includes a nonconductive material or fabric 12, flexible conductive fabric patches 14 attached to the nonconductive material 12, and a disposable gel 16. Straps 20, 22 provide a means for positioning and holding the nonconductive fabric 12 against a body part, such as an arm 28, as shown in FIG. 5.

As will be discussed hereinafter in greater detail, lead wires 30, electrically connected to each flexible conductive patch 14, provide a means for connecting the patches to one another or to a remotely disposed monitor or electrical stimulator (not shown). The patch 14 may be formed from any suitable conductive material or fabric.

Figure 1:
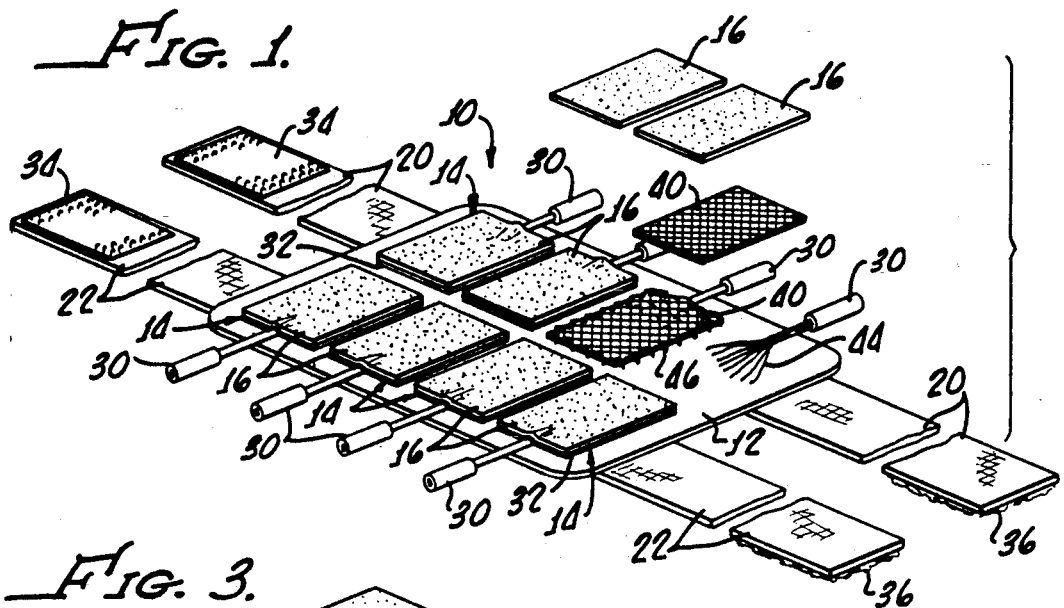
FIG. 1 is a perspective view of an electrode system in accordance with the present invention.
Figure 2:
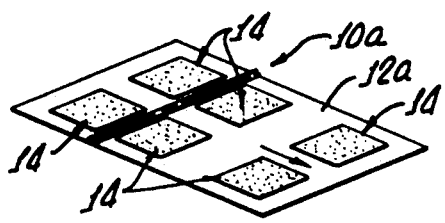
FIG. 2 is an alternative embodiment of the present invention showing a variation of patch placement enabled by an elastic substrate.

While a plurality of conductive fabric patches are shown in FIGS. 1 and 2, a single patch may be utilized depending upon the circumstances of treatment. The array of patches shown in FIG. 1 is only representative in nature. However, it is important to note that the fixing of the conductive fabric patches 14 to the nonconductive fabric 12 overcomes the problem associated with using multiple sets of electrodes. A spaced apart, fixed positioning of the electrode eliminates the cumbersome and unwieldy necessity of separate attachment of electrodes to a body. In addition, with single or smaller sets of electrodes, migration during prolonged stimulation or monitoring may occur and thus cause difficulty in ensuring consistent placement of the electrodes with respect to one another.

This is important, particularly with the placement of monitoring electrodes where the visual display of a patient's heart condition may be distorted due to improper placement of the monitoring electrodes.

More particularly, the nonconductive fabric 12, in accordance with the present invention, may be formed from any suitable material which is preferably machine washable. The function of the nonconductive fabric 12 is to provide a support for the conductive patches 14 and, at the same time, prevent any unwanted electrical communication between the electrodes or contact with the electrodes when the patches are placed in contact with the body.

While not required by the present invention, a barrier layer 32 may be provided over the nonconductive fabric 12, i.e., between the lead wire 30 and the fabric 12, in order to prevent the entry of moisture as may be present in the environment of use.

The straps 20, 22 are preferably sewn to the fabric 12 and are preferably formed from an elastic material. As shown, the straps 20, 22 may be secured on a body by means of a hook 34 and pile 36 arrangement, as is well known in the art. Alternatively, a belt configuration (not shown) may be utilized. The purpose of the straps 20, 22 are to ensure contact of the patches 14 with the gel 16 over a long duration of time.

In addition, the straps provide a means for compressing the body part as may be advantageous for use with sports injuries, for example. Also when properly sized, such compression straps 20 may be useful for support of a body part, such as for example, a low back support.

In muscle stimulation applications, the electrodes have a tendency to migrate and hence prior art utilization of multiple separate electrodes requires constant monitoring in order to insure proper placement of the electrodes. The present invention overcomes this disadvantage by maintaining proper relative placement of multiple electrodes.

In an alternative embodiment 10a of the present invention shown in FIG. 2, an elastic nonconductive fabric 12a may be utilized. This embodiment 10a may be more suitable for monitoring applications in which the conductive patches 14 may be positionally adjusted with one another in order that a variation in patient size may be accommodated even though the patches 14 are sewn to the elastic fabric 12a.

Thus the patches 14 may be placed farther apart, or closer together, on a body than their original sewn position on the fabric 12a.

The conductive fabric patches 14 may be formed from any suitable flexible, conductive fabric or material, but preferably are formed from a stretchable conductive material such as that described in U.S. Pat. Nos. 4,708,149 and 4,722,354, which are incorporated herewith in toto by specific reference thereto. In addition, the patches 14 may incorporate specific wire patterns to provide impedance compensation as described in U.S. Pat. No. 5,038,796, which is incorporated herewith in toto by specific reference thereto.

Conductivity of the fabric patches is provided by individual conductive fibers 40. A particularly suitable fiber is one manufactured by Bekaert of West Germany. This fiber, a blend of 20% 316 stainless steel and 80% polyester, can be latch-needle, honeycomb knitted to a density of about 3.5 lbs. per sq. yd., producing a conductive, double-stretch knit. Naturally, other conductive fabrics may be utilized in the present invention. The fabric patches may be sewn onto the nonconductive fabric 12, as shown in FIG. 1. Alternatively, if a suitable adhesive is used, the fabric patches 14 may be glued to the nonconductive fabric 12.

Because the patches 14 are also machine washable, along with the fabric 12 and the straps 20, 22, the entire electrode may be cleaned and reused, which provides favorable cost benefits to the patient undergoing long term treatment.

As also shown in FIG. 1, the lead wire comprises a plurality of connective strands 44 which may be of stainless steel. As shown in FIG. 1, the strands may be sewn in place onto the conductive patches 14 before the latter is sewn to the nonconductive fabric 12. The strands 44 may be fanned if necessary to provide more intimate contact with the fabric 12. The compression, upon sewing of the strands 44, to the conductive patches 14 provides sufficient electrical contact therebetween to enable electrical impulses to be distributed over the entire area of patch 14. In addition, the strands 44 may be sewn with conductive thread 46 to enhance electrical conductivity between the lead wire 30 and patch 14.

Alternatively, in a monitoring mode, the patch 14 utilizes the entire area as a receptor for receiving electrical pulses from a body.

The sewing of the lead wire is facilitated by utilizing a large plurality of strands, such as for example, about 1000 to about 1200 strands of 8 micron stainless steel. Alternatively, the strands 44 may be adhered to the conductive patches with a suitable conductive glue thereby enabling the assembly of the electrode without any sewing steps.

Figure 3:
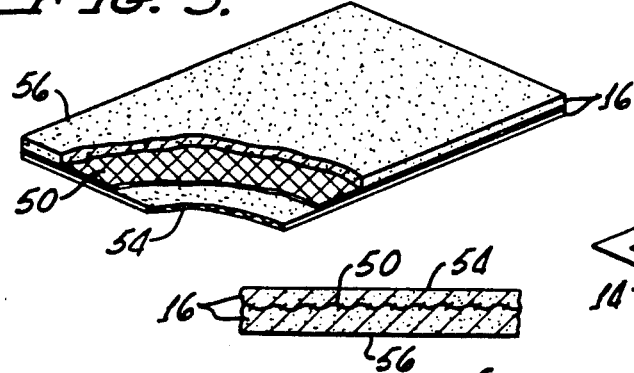
FIG. 3 is a perspective view, partially broken away, of a gel pad in accordance with the present invention.

Turning now to FIGS. 3 and 4, there is shown a disposable gel pad 16 in accordance with the present invention, which should be formed in a sufficient size to cover the patches 14 but not overlap with adjacent fabric patches.

A suitable conductive gel adhesive 16 is manufactured by Valleylab, Inc. of Boulder, Colo., under the name "Polyhesive ®". The pads 16 may be formed by pouring a liquid gel over a porous mesh 50 and thereafter allowing the material to set into a gel-like material. The mesh may be any suitable knit, open weave, woven or nonwoven material, enabling the gel to flow thereinto. The mesh may or may not be in and of itself a conductor of electricity. Importantly, it has been found that when the flexible mesh 50 is disposed closer to the surface 54, then another opposing surface 56 of the gel pad 16 means are provided for enabling the electrically conductive gel pad 16 to adhere more to the body part 28 than to the flexible conductive fabric patch 14, thereby enabling the flexible conductive patch 14 and the attached nonconductive fabric 12 to be removed from the body part 28 while leaving the electrically conductive gel pad adhered to the body part 28.

In accordance with the present invention, the gel pad may have an overall thickness of between about 0.020 inches and about 0.100 inches, with the mesh 50 disposed from about 0.005 to about 0.010 inches from the one side 54 of the pad 16. The mesh 50 may have a thickness in the order of about 0.004 inches.

Figure 6:
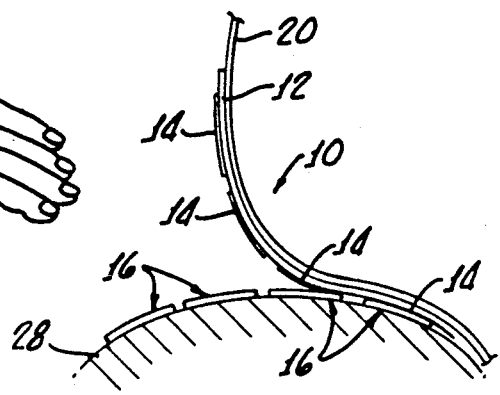
FIG. 6 is a figure showing preferential release of the gel pad from the conductive fabric patch while leaving the disposable gel pad on the skin of the user.

This configuration importantly enables the patches 14 and fabric 12 to be removed from the gel as shown in FIG. 6, thereby facilitating reuse of the patches 14 and fabric 12 without the necessity of scraping or removing gel therefrom. In addition, in prolonged use, as hereinabove mentioned, the patches and support fabric 12 may be washed as necessary between use.

Figure 7:
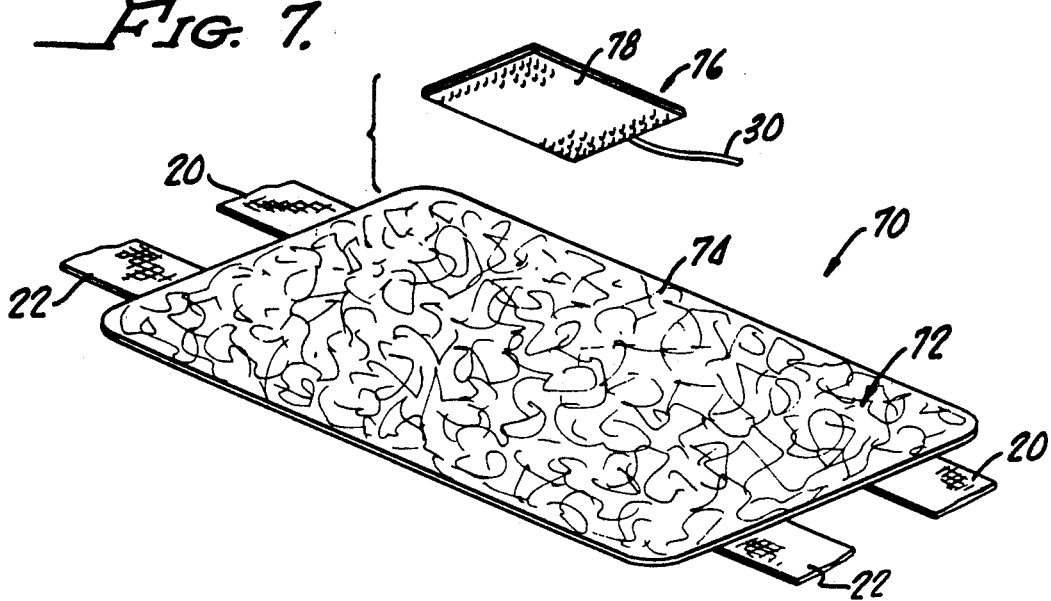
FIGS. 7-8 show an alternative embodiment of the present invention in which a hook and pile arrangement enables attachment and removal of conductive patches to a nonconductive substrate or material.
Figure 8:
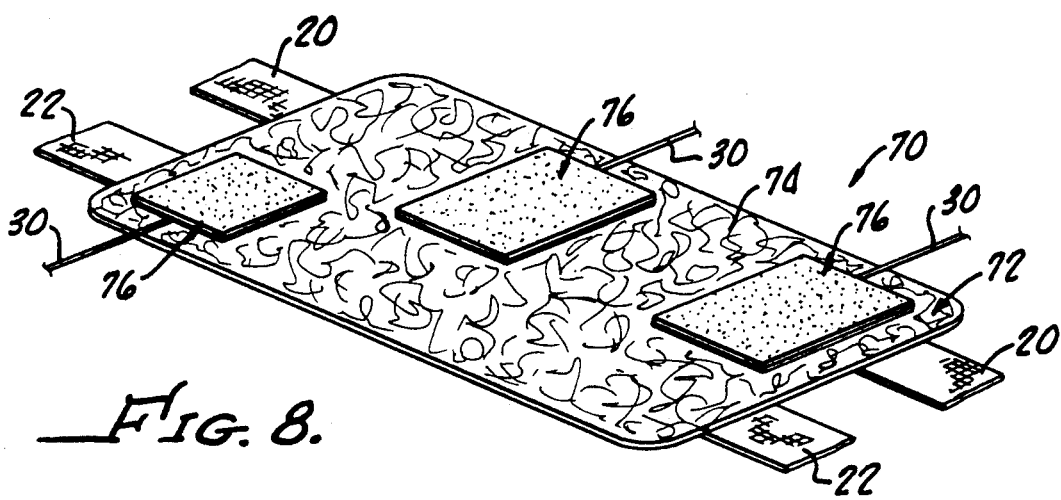
Figure 9:
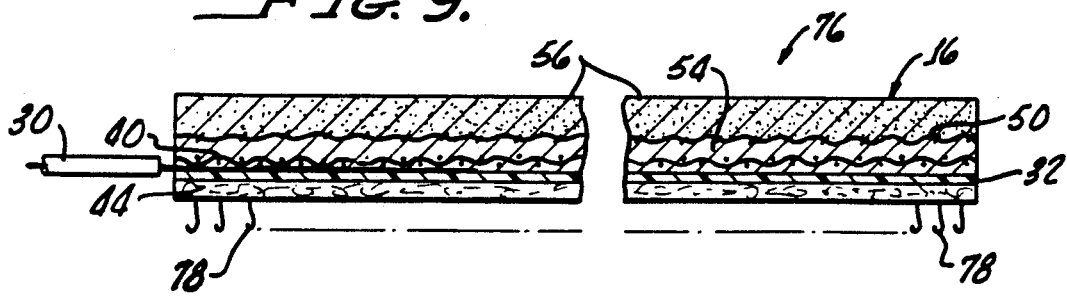
FIG. 9 is a cross-section of a conductive patch in accordance with the embodiment shown in FIGS. 7-8.

Yet another embodiment 70 of the present invention is shown in FIGS. 7 to 9. In this embodiment 70, a nonconductive substrate 72 includes a pile material 74, and flexible conductive patches 76 include a hook material 78 to enable the patches 76 to be placed and removed from the substrate 72. The pile and hook materials may be any commonly known fastening system typically referred to as a Velcro fastener. In this embodiment, the patches 76 need not be washable since they can be removed from the substrate 72, which then can be separately cleansed.

As shown, the patches 76 may be of a variety of shapes and sizes to accommodate various stimulation or monitoring needs.

In FIGS. 7 to 9, like reference numerals or characters refer to identical or corresponding parts throughout the several views. In this embodiment, the barrier layer 32 also provides integrity to the patch 76 for enabling repeated attachment and removal of the patch 76 from the substrate 72.

The disposable gel 16 has been hereinabove described and may include a porous mesh 50 to both provide integrity to the gel and control its adhesive characteristics as hereinabove described in detail.

Also, as hereinabove described, the lead wires 30 may be either sewn or glued to the conductive patches 76.

In a method in accordance with the present invention, the one side 54 of the electrically conductive adhesive gel pad is adhered to the electrically conductive patches 14. Thereafter, the conductive patches are coupled to a body part by adhering the other side 56 of the gel pad against the body part 28. Following the positioning of the patches 14 on the body part, the straps 20 and 22 may be secured by the Velcro 34 and felt 36 on the body part. Electrical connection is then made with a remote electrical pulse generator or receiver through the electrical lead wires 30.

Securing of the straps 20, 22 prevent migration of the conductive fabric patch, conductive adhesive gel along the body part 28 during application and/or detection of electrical pulses. After a treatment period, the conductive fabric patch is removed from the gel pad 16, leaving the conductive gel patch 16 on the body part, saving the conductive fabric patch for later use.

Finally, the gel pad 16 is removed from the body part 28 and disposed.

Although there has been hereinabove described a specific arrangement of an electrode system with disposable gel and method in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. An electrode system comprising:
   a nonconductive material;
   means for positioning and supporting said nonconductive material against a body part;
   a flexible conductive patch attached to said nonconductive material;
   a lead wire electrically connected to said flexible conductive patch; and
   electrically conductive gel means for releasably coupling said flexible conductive patch to said body part, said electrically conductive gel means being removable form said flexible conductive patch, said electrically conductive gel means comprises means for causing said electrically conductive gel means to adhere more to the body part than to the flexible conductive patch, thereby enabling the flexible conductive patch and attached nonconducting material to be removed from the body part, while leaving the electrically conductive gel means adhered to the body part.

2. The electrode system according to claim 1 comprising a plurality of flexible conductive patches attached to said nonconductive material in a spaced apart array with each patch having a separate lead wire attached thereto.

3. The electrode system according to claim further comprising a moisture barrier disposed between said lead wire and the nonconductive material.

4. The electrode system according to claim 1 wherein said means for causing said electrically conductive gel means to adhere more to the body part comprises a flexible mesh disposed within said electrically conductive gel means.

5. The electrode system according to claim 4 wherein said flexible mesh is disposed within said electrically conductive gel means closer to one surface than another opposing surface, said one surface being used to adhere to gel means to said flexible conductive patch.

6. The electrode system according to claim 5 wherein said flexible mesh comprises a nonconductive material having interstitial means for supporting electrically conductive gel means thereon.

7. The electrode system according to claim 7 wherein said flexible conductive patch is sewn to said nonconductive material.

8. The electrode system according to claim 7 wherein said lead wire comprises means for facilitating sewing thereof to the conductive patch with electrical contact therebetween being sustained by the sewing.

9. The electrode system according to claim 8 wherein said means for facilitating sewing comprises a plurality of electrically conductive strands, said strands being sewn to the flexible conductive patch.

10. An electrode system comprising:
    a nonconductive pile material;
    means for positioning and supporting said nonconductive material against a body part;
    a flexible conductive patch including hook material means for removably attaching said flexible conductive patch to said nonconductive pile material;
    a lead wire electrically connected to said flexible conductive patch; and
    electrically conductive gel means for releasably coupling said flexible conductive patch to said body part, said electrically conductive gel means being removable from said flexible conductive patch,
    said electrically conductive gel means comprises means for causing said electrically conductive gel means to adhere more to the body part than to the flexible conductive patch, thereby enabling the flexible conductive patch and attached nonconducting material to be removed from the body part, while leaving the electrically conductive gel means adhered to the body part.

11. The electrode system according to claim 10 wherein said means for causing said electrically conductive gel means to adhere more to the body part comprises a flexible mesh disposed within said electrically conductive gel means.

12. The electrode system according to claim 11 wherein said flexible mesh is disposed within said electrically conductive gel means closer to one surface than another opposing surface, said one surface being used to adhere the gel means to said flexible conductive patch.

13. The electrode system according to claim 12 wherein the nonconductive material is washable.

14. An electrode system comprising:
    a nonconductive fabric;
    means attached to said nonconductive fabric for positioning and compressing said nonconductive fabric against a body part;
    a plurality of flexible conductive fabric patches attached to said nonconductive fabric;
    a lead wire electrically connected to said flexible conductive fabric patches; and
    a plurality of disposable, electrically conductive gel means for releasably coupling said flexible conductive fabric patch to said body part; said electrically conductive gel means being removable from said flexible conductive fabric patch, said electrically conductive gel means comprises means for causing said electrically conductive gel means to adhere more to the body part than to the flexible conductive fabric patch, thereby enabling the flexible conductive fabric patch and attached nonconducting fabric to be removed from the body part, while leaving the electrically conductive gel means adhered to the body part.

15. The electrode system according to claim 14 further comprising a moisture barrier disposed between said lead wire and the nonconductive fabric.

16. The electrode system according to claim 14 comprising a plurality of flexible conductive fabric patches attached to said nonconductive fabric in a spaced apart array with each fabric patch having a separate lead wire attached thereto.

17. The electrode system according to claim 14 wherein said means for causing said electrically conductive gel means to adhere more to the body part comprises a flexible mesh disposed within said electrically conductive gel means.

18. The electrode system according to claim 17 wherein said flexible mesh is disposed within said electrically conductive gel means closer to one surface than another opposing surface, said one surface being used to adhere the gel means to said flexible conductive fabric patch.

19. The electrode system according to claim 18 wherein said flexible mesh comprises a nonconductive material having interstitial means for supporting electrically conductive gel means thereon.

20. The electrode system according to claim 18 wherein said flexible conductive fabric patch is sewn to said nonconductive fabric.

21. The electrode system according to claim 18 wherein said lead wire comprises a plurality of electrically conductive strands and the strands are sewn to the flexible conductive fabric patch.

22. A method for applying and/or detecting electrical pulses in an animal body comprising the steps of:

(a) applying one side of an electrically conductive adhesive gel pad to an electrically conductive fabric patch;

(b) coupling the conductive fabric patch to a body part by adhering another side of the conductive adhesive gel pad against a body part;

(c) electrically connecting the conductive fabric patch with an electrical pulse generator and/or receiver;

(d) preventing migration of the conductive fabric patch and conductive adhesive gel pad along said body part during application and/or detection or electrical pulses;

(e) removing the conductive fabric patch from the conductive adhesive gel pad leaving the conductive adhesive gel pad on said body part and saving the conductive fabric patch for later use according to hereinabove steps (a)-(d);

(f) removing and disposing of the conductive adhesive gel pad.

23. The method according to claim 22 further comprising the step of cleaning the conductive fabric patch before later use according to steps (a)-(d) of claim 22.

* * * * *